United States Patent
Wisniewski

(10) Patent No.: US 9,707,556 B2
(45) Date of Patent: Jul. 18, 2017

(54) DEVICE, SYSTEM AND METHOD FOR PROCESSING A SAMPLE

(75) Inventor: Craig Wisniewski, Cambridgshire (GB)

(73) Assignee: Diagnostics for the Real World, LTD., Sunnyvale, CA (US)

( * ) Notice: Subject to any disclaimer, the term of this patent is extended or adjusted under 35 U.S.C. 154(b) by 686 days.

(21) Appl. No.: 12/673,939

(22) PCT Filed: Aug. 18, 2008

(86) PCT No.: PCT/GB2008/002802
§ 371 (c)(1),
(2), (4) Date: Mar. 3, 2011

(87) PCT Pub. No.: WO2009/024773
PCT Pub. Date: Feb. 26, 2009

(65) Prior Publication Data
US 2011/0143339 A1     Jun. 16, 2011

(30) Foreign Application Priority Data

Aug. 17, 2007 (GB) .................................. 0716156.5
Aug. 8, 2008 (GB) .................................. 0814550.0

(51) Int. Cl.
*G01N 1/10* (2006.01)
*B01L 3/00* (2006.01)
(Continued)

(52) U.S. Cl.
CPC ........... *B01L 3/5027* (2013.01); *B01L 3/5023* (2013.01); *B01L 9/527* (2013.01); *B01L 2200/0642* (2013.01); *B01L 2200/10* (2013.01); *B01L 2200/12* (2013.01); *B01L 2200/16* (2013.01); *B01L 2300/049* (2013.01); *B01L 2300/0636* (2013.01); *B01L 2300/087* (2013.01);
(Continued)

(58) Field of Classification Search
None
See application file for complete search history.

(56) References Cited

U.S. PATENT DOCUMENTS 3,660,033 A   5/1972   Schwartz
3,689,224 A   9/1972   Agnew et al.
(Continued)

FOREIGN PATENT DOCUMENTS

DE   103 31 108       2/2005
EP   0 291 194 B1    11/1988
(Continued)

OTHER PUBLICATIONS

Chiou; "DNA-Scission Activities of Ascorbate in the Presence of Metal Chelates;" J. Biochem, vol. 96, No. 4, 1984; pp. 1307-1310.
(Continued)

*Primary Examiner* — Robert Xu
(74) *Attorney, Agent, or Firm* — Daly, Crowley, Mofford & Durkee, LLP

(57) ABSTRACT

A device for processing a sample comprises a blister defined by first and second walls. The first wall is flexible allowing the blister to be divided into one or more sealed regions by an external pressure applied to a portion of the first wall. The external pressure is applied in the form of a 2-dimensional shape to form a sealed region having that shape.

24 Claims, 13 Drawing Sheets

(51) Int. Cl.
*B01L 9/00* (2006.01)
*G01N 35/00* (2006.01)

(52) U.S. Cl.
CPC .......... *B01L 2300/0816* (2013.01); *B01L 2300/0825* (2013.01); *B01L 2300/0887* (2013.01); *B01L 2300/123* (2013.01); *B01L 2300/1827* (2013.01); *B01L 2400/049* (2013.01); *B01L 2400/0481* (2013.01); *B01L 2400/0638* (2013.01); *G01N 2035/00366* (2013.01); *G01N 2035/00534* (2013.01)

(56) References Cited

U.S. PATENT DOCUMENTS

| | | | |
|---|---|---|---|
| 3,713,779 | A | 1/1973 | Sirago et al. |
| 4,065,263 | A | 12/1977 | Woodbridge, III |
| 4,765,810 | A * | 8/1988 | Wetzel ............... 96/417 |
| 4,795,265 | A | 1/1989 | Dahlberg et al. |
| 4,978,602 | A | 12/1990 | Fujita et al. |
| 5,035,996 | A | 7/1991 | Hartley |
| 5,089,233 | A | 2/1992 | DeVaney, Jr. et al. |
| 5,096,669 | A | 3/1992 | Lauks et al. |
| 5,116,576 | A | 5/1992 | Stanley |
| 5,154,888 | A | 10/1992 | Zander et al. |
| 5,229,297 | A | 7/1993 | Schnipelsky et al. |
| 5,267,648 | A | 12/1993 | Baker |
| 5,288,463 | A | 2/1994 | Chemelli |
| 5,310,523 | A | 5/1994 | Smethers et al. |
| 5,422,271 | A | 6/1995 | Chen et al. |
| 5,460,780 | A | 10/1995 | Devaney, Jr. et al. |
| 5,538,849 | A | 7/1996 | Uematsu et al. |
| 5,599,501 | A | 2/1997 | Carey et al. |
| 5,602,040 | A | 2/1997 | May et al. |
| 5,604,101 | A | 2/1997 | Hanley et al. |
| 5,622,871 | A | 4/1997 | May et al. |
| 5,645,801 | A | 7/1997 | Bouma et al. |
| 5,656,503 | A | 8/1997 | May et al. |
| 5,714,380 | A | 2/1998 | Neri et al. |
| 5,714,389 | A | 2/1998 | Charlton et al. |
| 5,725,831 | A | 3/1998 | Reichler et al. |
| 5,783,148 | A | 7/1998 | Cottingham et al. |
| 5,811,296 | A | 9/1998 | Chemelli et al. |
| 5,824,216 | A | 10/1998 | Joie et al. |
| 5,827,478 | A | 10/1998 | Carey et al. |
| 5,843,793 | A | 12/1998 | Belly et al. |
| 5,849,544 | A | 12/1998 | Harris et al. |
| 5,863,502 | A | 1/1999 | Southgate et al. |
| 5,910,138 | A | 6/1999 | Sperko et al. |
| 5,922,288 | A | 7/1999 | Herst |
| 5,922,591 | A | 7/1999 | Anderson et al. |
| 5,935,858 | A | 8/1999 | Herst |
| 5,948,673 | A | 9/1999 | Cottingham |
| 5,955,351 | A | 9/1999 | Gerdes et al. |
| 5,989,499 | A | 11/1999 | Catanzariti et al. |
| 5,989,921 | A | 11/1999 | Charlton et al. |
| 6,007,529 | A | 12/1999 | Gustafsson et al. |
| 6,043,080 | A | 3/2000 | Lipshutz et al. |
| 6,077,711 | A | 6/2000 | Singer |
| 6,153,425 | A | 11/2000 | Kozwich et al. |
| 6,162,602 | A | 12/2000 | Gautsch |
| 6,187,598 | B1 | 2/2001 | May et al. |
| 6,228,660 | B1 | 5/2001 | May et al. |
| 6,247,617 | B1 | 6/2001 | Clyde et al. |
| 6,251,660 | B1 | 6/2001 | Muir et al. |
| 6,300,068 | B1 | 10/2001 | Burg et al. |
| 6,300,142 | B1 | 10/2001 | Andrewes et al. |
| 6,318,191 | B1 | 11/2001 | Chen |
| 6,319,243 | B1 | 11/2001 | Becker et al. |
| 6,395,227 | B1 | 5/2002 | Kiser et al. |
| 6,398,771 | B1 | 6/2002 | Gustafsson et al. |
| 6,410,275 | B1 | 6/2002 | Kluttz et al. |
| 6,426,230 | B1 | 7/2002 | Feistel |
| 6,429,007 | B1 | 8/2002 | Kluttz et al. |
| 6,468,377 | B1 | 10/2002 | Sperko et al. |
| 6,485,982 | B1 | 11/2002 | Charlton |
| 6,565,808 | B2 | 5/2003 | Hudak et al. |
| 6,586,234 | B1 | 7/2003 | Burg et al. |
| 6,645,758 | B1 | 11/2003 | Schnipelsky et al. |
| 6,649,378 | B1 | 11/2003 | Kozwich et al. |
| 6,663,743 | B1 | 12/2003 | Becker et al. |
| 6,713,298 | B2 | 3/2004 | McDevitt et al. |
| 6,748,332 | B2 | 6/2004 | Chen |
| 6,764,567 | B2 | 7/2004 | Sperko et al. |
| 6,780,617 | B2 | 8/2004 | Chen |
| 6,818,455 | B2 | 11/2004 | May et al. |
| 6,846,305 | B2 | 1/2005 | Smith et al. |
| 6,872,566 | B2 | 3/2005 | Vischer et al. |
| 6,921,639 | B2 | 7/2005 | Vischer |
| 6,949,376 | B2 | 9/2005 | Kluttz et al. |
| 6,964,862 | B2 | 11/2005 | Chen |
| 6,996,951 | B2 | 2/2006 | Smith et al. |
| 7,033,761 | B2 | 4/2006 | Shafer |
| 7,109,042 | B2 | 9/2006 | May et al. |
| 7,169,138 | B2 | 1/2007 | Becker et al. |
| 7,175,614 | B2 | 2/2007 | Gollier et al. |
| 7,214,529 | B2 | 5/2007 | Kluttz et al. |
| 7,241,417 | B2 | 7/2007 | Lee et al. |
| 7,270,959 | B2 | 9/2007 | Hudak |
| 7,544,324 | B2 | 6/2009 | Tung et al. |
| 7,560,272 | B2 | 7/2009 | Ramsey et al. |
| 7,758,815 | B2 | 7/2010 | Hartselle |
| 7,767,447 | B2 | 8/2010 | Breidenthal et al. |
| 8,017,340 | B2 | 9/2011 | Collier et al. |
| 8,018,593 | B2 | 9/2011 | Tan et al. |
| 8,062,884 | B2 | 11/2011 | Sarofim |
| 8,133,703 | B2 | 3/2012 | Ching et al. |
| 8,182,747 | B2 | 5/2012 | Marquant et al. |
| 8,394,608 | B2 | 3/2013 | Ririe et al. |
| 2002/0086309 | A1 | 7/2002 | Penn et al. |
| 2003/0012697 | A1 | 1/2003 | Hahn et al. |
| 2003/0049833 | A1 | 3/2003 | Chen et al. |
| 2003/0073089 | A1 | 4/2003 | Mauze et al. |
| 2003/0186295 | A1 | 10/2003 | Colin et al. |
| 2003/0224371 | A1 | 12/2003 | Thomas et al. |
| 2004/0161788 | A1 | 8/2004 | Chen et al. |
| 2004/0223878 | A1 | 11/2004 | Chen |
| 2004/0248087 | A1 | 12/2004 | Burg et al. |
| 2005/0009203 | A1 | 1/2005 | Wong |
| 2005/0153430 | A1 | 7/2005 | Ohtaka |
| 2005/0161377 | A1 | 7/2005 | Fujimoto et al. |
| 2005/0244308 | A1 | 11/2005 | Tanaami et al. |
| 2005/0244837 | A1 | 11/2005 | McMillan |
| 2005/0244887 | A1 | 11/2005 | Kluttz et al. |
| 2006/0019273 | A1 | 1/2006 | Connolly et al. |
| 2006/0023039 | A1 | 2/2006 | Padmanabhan et al. |
| 2006/0030038 | A1 | 2/2006 | Taylor et al. |
| 2006/0040405 | A1 | 2/2006 | Charlton et al. |
| 2006/0154341 | A1 | 7/2006 | Chen |
| 2006/0160078 | A1 | 7/2006 | Cardy et al. |
| 2006/0263871 | A1 | 11/2006 | Kluttz et al. |
| 2007/0065225 | A1 | 3/2007 | Moore |
| 2007/0154355 | A1 | 7/2007 | Berndt et al. |
| 2007/0154922 | A1 | 7/2007 | Collier et al. |
| 2007/0184547 | A1 | 8/2007 | Handique et al. |
| 2008/0153078 | A1 | 6/2008 | Braman et al. |
| 2008/0166279 | A1 | 7/2008 | Tanaami et al. |
| 2009/0017554 | A1 | 1/2009 | Vann |
| 2009/0074624 | A1 | 3/2009 | Liang |
| 2009/0227006 | A1 | 9/2009 | Kopp et al. |
| 2010/0003683 | A1 | 1/2010 | Sarofim et al. |
| 2010/0028204 | A1 | 2/2010 | Lee et al. |
| 2010/0144541 | A1 | 6/2010 | Murasato et al. |
| 2011/0104731 | A1 | 5/2011 | Teng et al. |
| 2011/0244466 | A1 | 10/2011 | Juncosa et al. |
| 2012/0040468 | A1 | 2/2012 | Khaled |

FOREIGN PATENT DOCUMENTS

| | | |
|---|---|---|
| EP | 0 349 215 B1 | 1/1990 |
| EP | 0 381 501 A2 | 8/1990 |
| EP | 0 402 994 A2 | 12/1990 |
| EP | 0 402 995 A2 | 12/1990 |
| EP | 0 560 410 B1 | 9/1993 |
| EP | 0 560 411 B1 | 9/1993 |

(56) References Cited

FOREIGN PATENT DOCUMENTS

| | | |
|---|---|---|
| EP | 0 606 961 B1 | 7/1994 |
| EP | 0 656 068 B1 | 6/1995 |
| EP | 0 712 000 | 5/1996 |
| EP | 0 838 025 B1 | 4/1998 |
| EP | 0 875 291 A2 | 11/1998 |
| EP | 0 898 466 B1 | 3/1999 |
| EP | 1 146 961 B1 | 10/2001 |
| EP | 1 146 963 B1 | 10/2001 |
| EP | 1 161 932 B1 | 12/2001 |
| EP | 1 248 112 A2 | 10/2002 |
| EP | 1 295 949 A1 | 3/2003 |
| EP | 1 371 419 | 12/2003 |
| EP | 0 541 715 B2 | 6/2004 |
| EP | 1 555 529 A2 | 7/2005 |
| EP | 1 614 464 | 1/2006 |
| EP | 1 614 464 A1 | 1/2006 |
| EP | 1 792 654 A2 | 6/2007 |
| EP | 1 798 556 A1 | 6/2007 |
| EP | 2 279 790 | 2/2011 |
| FR | 2 609 334 | 7/1988 |
| FR | 2 609 334 A1 | 7/1988 |
| GB | 2 283 318 A | 5/1995 |
| GB | 2 455 204 | 6/2009 |
| WO | WO 91/16086 | 10/1991 |
| WO | WO 91/19567 | 12/1991 |
| WO | WO 94/02634 | 2/1994 |
| WO | WO 98/40466 | 9/1998 |
| WO | WO 98/54580 | 12/1998 |
| WO | WO 99/28038 | 6/1999 |
| WO | WO 99/67646 | 12/1999 |
| WO | WO 01/41930 | 6/2001 |
| WO | WO 01/41930 A1 | 6/2001 |
| WO | WO 02/057798 A2 | 7/2002 |
| WO | WO 03/022435 A2 | 3/2003 |
| WO | WO 2004/012862 A2 | 2/2004 |
| WO | WO 2004/080597 A2 | 9/2004 |
| WO | WO 2005/005044 A1 | 1/2005 |
| WO | WO 2005/121963 A2 | 12/2005 |
| WO | WO 2006/018044 | 2/2006 |
| WO | WO 2006/018044 A1 | 2/2006 |
| WO | WO 2006/121997 A2 | 11/2006 |
| WO | WO 2006/136990 | 12/2006 |
| WO | WO 2008/012550 | 1/2008 |
| WO | WO 2008/012550 A2 | 1/2008 |
| WO | WO 2009/024773 A1 | 2/2009 |

OTHER PUBLICATIONS

Compton; "Nucleic Acid Sequence-based amplification;" Nature, vol. 350, Mar. 7, 1991; pp. 91-92.
Sigman, et al.; "Oxygen-dependent Cleavage of DNA by the 1,10-Phenanthroline Cuprous Complex;" The Journal of Biological Chemistry, vol. 254, No. 24, Dec. 1979; pp. 12269-12272.
Guatelli, et al.; Isothermal, in vitro amplification of nucleic acids by a multienzyme reaction modeled after retroviral replication; Proc. Natl. Acad. Sci.; Vo. 87; Mar. 1990; pp. 1874-1878.
PCT International Preliminary Report on Patentability and Written Opinion of the ISA for PCT/GB2008/002802 dated Mar. 4, 2010; 10 pages.
PCT Search Report of the ISA for PCT/GB2008/002802 dated Dec. 30, 2008; 3 pages.
Search Report of the GB IPO for GB/0716156.5 dated Apr. 28, 2008; 2 pages.
Further Search Report of the GB IPO for GB0716156.5 dated Jul. 7, 2008; 8 pages.
Response to Office Action filed Feb. 4, 2015 for U.S. Appl. No. 12/673,939; 20 pages.
Response to Office Action, Request for Continued Examination filed Oct. 1, 2015 U.S. Appl. No. 12/673,939; 12 pages.
Office Action dated May 23, 2011; for U.S. Appl. No. 12/375,335; 17 pages.
Response filed Sep. 1, 2011; to Office Action dated May 23, 2011; for U.S. Appl. No, 12/375,335; 9 pages.
Notice of Non-Compliant Amendment dated Dec. 13, 2011; for U.S. Appl. No. 12/375,335; 2 pages.
Response filed Dec. 27, 2013; to Notice of Non-Compiient Amendment dated Dec. 13, 2011; for U.S. Appl. No. 12/375,335. 8 pages.
Final Office Action dated Apr. 6, 2012; for U.S. Appl. No. 12/375,335; 12 pages.
Response filed Oct. 4, 2012; to Final Office Action dated Apr. 6, 2012; for U.S. Appl. No. 12/375,335; 10 pages.
Office Action dated Aug. 4, 2014 for U.S. Appl. No. 12/375,335, filed Sep. 29, 2009 14 pages.
Instruction letter from client dated Jul. 4, 2014 to respond to the re-examiniation notice and amend claims; for Chinese Application No. 200780036383.6; 1 page.
Instruction letter from client dated Apr. 30, 2015 to respond to the re-examinaton notice and amend claims; for Chinese Application No. 200780036383.6; 3 pages.
European Examination Report dated May 6, 2009 for European Application No. 0904302.7; 3 pages.
European Response to Examination Report filed Sep. 7, 2009 for European Application No. 0904302.7; 10 pages.
European Examination Report dated Sep. 24, 2009 for European Application No. 0904302.7; 3 pages.
European Response to Examination Report filed Nov. 24, 2009 for European Application No. 0904302.7; 12 pages.
European Examination Report dated Dec. 24, 2009 for European Application No. 0904302.7; 3 pages.
European Response to Examination Report filed Feb. 24, 2010 for European Application No. 0904302.7; 17 pages.
Office Action dated Apr. 12, 2013 for U.S. Appl. No. 12/375,335; 8 pages.
Response to Office Action filed Oct. 11, 2013 U.S. Appl. No. 12/375,335; 10 pages.
Office Action dated Dec. 18, 2013 for U.S. Appl. No. 12/375,335; 10 pages.
Response to Office Action filed Jun. 17, 2014 U.S. Appl. No. 12/375,335; 10 pages.
Response to Office Action filed Oct. 1, 2015 U.S. Appl. No. 12/375,335; 17 pages.
English Translation of Decision of Rejection dated Nov. 26, 2012 for Chinese Application No. 200780036383.6; 3 pages.
Notification of Transmittal of the International Search Report and the Written Opinion of the International Searching Authority, PCT/GB2007/002854 dated Mar. 17, 2008.
Notification of International Preliminary Report on Patentability and Written Opinion of the International Searching Authority for PCT/GB2007/002854, dated Feb. 12, 2009, 9 pages.
PCT/GB2008/002802 filed Aug. 18, 2008 Written Opinion.
U.S. Final Office Action dated Apr. 2, 2015 corresponding to U.S. Appl. No. 12/375,335; 11 Pages.
U.S. Office Action dated Mar. 24, 2016 corresponding to U.S. Appl. No. 12/375,335; 15 Pages.
GB Report dated May 6, 2009 for GB Application No. 0904302.7; 3 pages.
GB Response to Examination Report filed Sep. 7, 2009 for GB Application No. 0904302.7; 10 pages.
GB Examination Report dated Sep. 24, 2009 for GB Application No. 0904302.7; 3 pages.
GB Response to Examination Report filed Nov. 24, 2009 for GB Application No. 0904302.7; 12 pages.
GB Examination Report dated Dec. 24, 2009 for GB Application No. 0904302.7; 3 pages.
GB Response to Examination Report filed Feb. 24, 2010 for GB Application No. 0904302.7; 17 pages.
English Translation of Chinese Office Action dated Apr. 19, 2011 for Chinese Application No. 200780036383.6; 4 pages.
English Translation of Chinese Office Action dated Apr. 19, 2012 for Chinese Application No. 200780036383.6; 1 page.
English Translation of Decision of Rejection dated Jan. 24, 2013 for Chinese Application No. 200780036383.6; 3 pages.
English Translation of Chinese Office Action dated Mar. 27, 2014 for Chinese Application No. 200780036383.6; 3 pages.

(56) References Cited

OTHER PUBLICATIONS

English Translation of Chinese of Re-examination decision dated Jun. 4, 2015 for Chinese Application No. 200780036383.6; 4 pages.
European Office Action dated Mar. 20, 2012 for European Application No. 07766370.6; 12 pages.
Response to European Office Action filed Sep. 28, 2012 for European Application No. 07766370.6; 10 pages.
European Office Action dated Oct. 15, 2013 for European Application No. 07766370.6; 5 pages.
Response to European Office Action filed Jul. 29, 2014 for European Application No. 07766370.6; 10 pages.
European Office Action dated Mar. 18, 2016 for European Application No. 07766370.6; 3 pages.
UK Search Report dated Jan. 5, 2007 for UK Application 0615110.4; 5 pages.
UK Office Action dated Jun. 1, 2010 for UK Application 0615110.4; 3 pages.
Response to UK Office Action filed Jul. 30, 2010 for UK Application No. 0615110.4; 9 pages.
UK Office Action dated Sep. 22, 2010 for UK Application 0615110.4; 4 pages.
UK Response to European Office Action filed Jan. 21, 2011 for UK Application No. 0615110.4; 13 pages.
UK Office Action dated Apr. 15, 2011 for UK Application 0615110.4; 3 pages.
Response to UK Office Action filed May 13, 2011 for UK Application No. 0615110.4; 12 pages.
Instruction letter from client dated Oct. 28, 2011 (including English claims) to file response to Examiner's Office Action; for Chinese Application No. 200780036383.6; 9 pages.
Email dated Nov. 3, 2011 from Foreign Associate with proposed amendment to claims 1 and 35; for Chinese Application No. 200780036383.6; 1 page.
Instruction letter from client dated May 16, 2012 (including English comments to claims) to file response to Examiner's Office Action; for Chinese Application No. 200780036383.6; 2 pages.
Instruction letter from client dated Feb. 26, 2013 to request re-examination and amend claims; for Chinese Application No. 200780036383.6; 1 page.
Instruction letter from client dated Jul. 4, 2014 to respond to the re-examination notice and amend claims; for Chinese Application No. 200780036383.6; 1 page.
Instruction letter from client dated Apr. 30, 2015 to respond to the re-examination notice and amend claims; for Chinese Application No. 200780036383.6; 3 pages.
English Translation of Chinese $2^{nd}$ Re-examination Notification dated Mar. 27, 2014 for Chinese Application No. 200780036383.6; 6 pages.
Written Opinion dated Feb. 24, 2010 for PCT Application No. PCT/GB2008002802; 8 pages.
Final Office Action dated Dec. 29, 2016 for U.S. Appl. No. 12/375,335; 8 pages.
Response to Final Office Action filed on Mar. 29, 2017 for U.S. Appl. No. 12/375,335; 9 pages.

\* cited by examiner

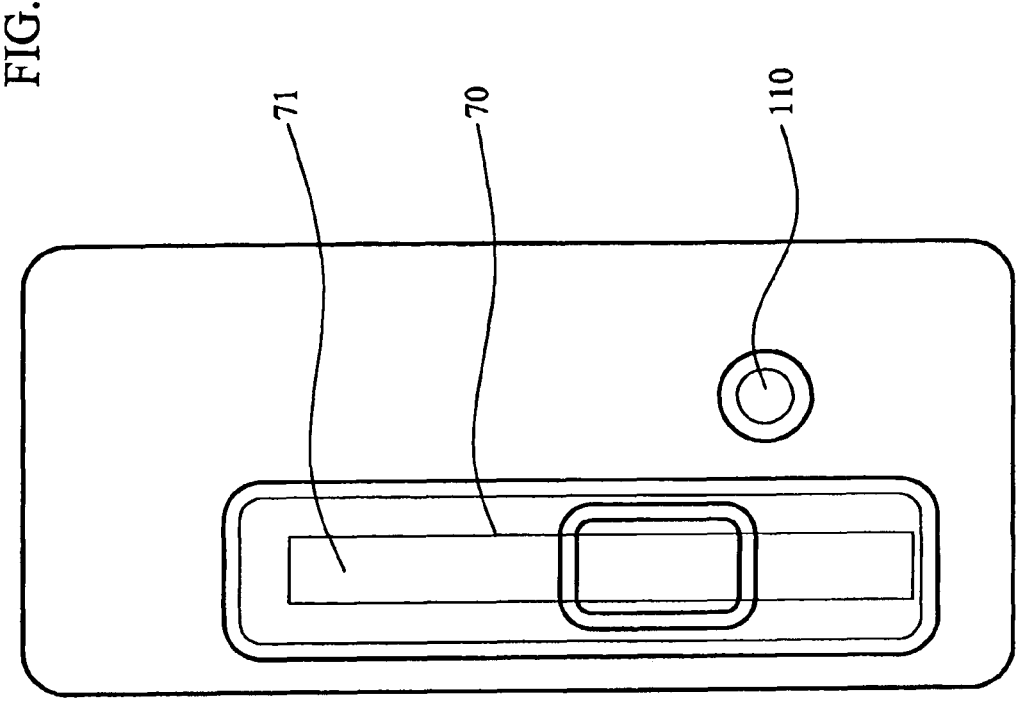
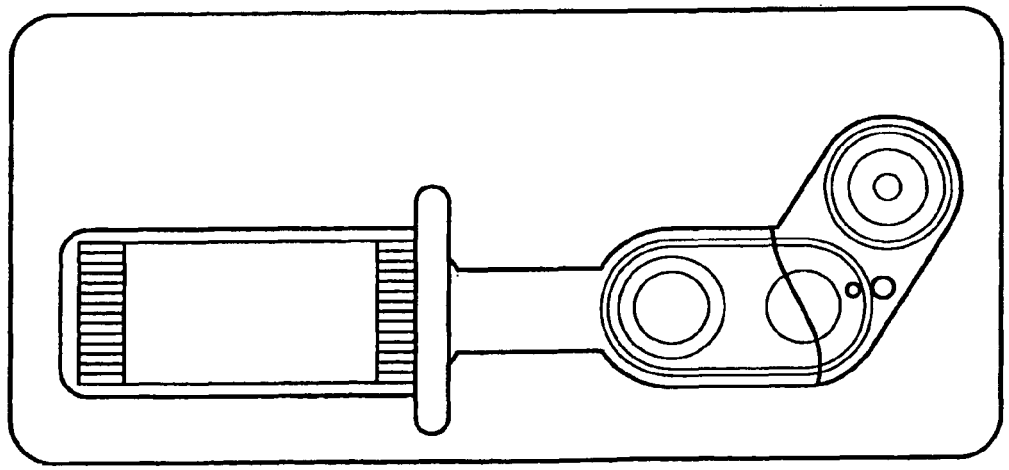

DEVICE, SYSTEM AND METHOD FOR PROCESSING A SAMPLE

CROSS REFERENCE TO RELATED APPLICATION

This application claims the benefit of International Patent Application PCT/GB2008/002802 filed Aug. 18, 2008 published in the English language as WO2009/024773, which application claims priority from GB application number GB0814550.0, filed Aug. 8, 2008 and GB application number GB0716156.5, filed on Aug. 17, 2007.

The invention relates to devices, a system and a method for the processing of a sample. In particular the invention relates to in-the-field and on-site analysis of nucleic acid or genetic material in a biological or environmental sample.

BACKGROUND

The importance of nucleic acid testing (NAT) has become increasingly evident during the last decade for many purposes such as screening and diagnosis of infectious diseases and genetic disorders, testing for disease susceptibility, therapy monitoring, and improving the safety of blood supplies. NAT combines the advantages of direct and highly sequence-specific detection of the genome of an infectious agent with an analytic sensitivity that is several orders of magnitude greater than that of immuno-based tests, or virus isolation and cell culture methods. Due to the high sensitivity of NAT, its use in blood banks reduces the risk of infectious agent transmission during the period between infection and seroconversion, of infection with immunovariant viruses, of immunosilent or occult carriage. NAT-based assays consist of three basic steps: extraction of nucleic acid, genome amplification mediated by procedures such as (RT)-PCR; strand-displacement amplification (SDA) and transcription-based amplification system TAS (Guatelli et al., Proc. Natl. Acad. Sci. 87: 1874-1878 (1990); Compton, Nature 350: 91-92 (1991)), and amplicon detection.

Currently available NAT assays are complex and entail multi-step procedures that require highly trained personnel and specialised facilities. They require cold-chain transport and storage of reagents, a high investment cost for instruments, high running costs for reagents, and regular maintenance support. All of these restrict the use of NAT only to specialized well-equipped and technically advanced laboratories. Correspondingly, current NAT assay design is unsuitable for near-patient and field-testing e.g. physician's office, community-based clinics, emergency rooms, battlefield surgery units or point-of care health centres, district hospitals and inner-city clinics in the resource-limited settings of developing countries. These include predominantly countries of Africa, Asia, and Latin America with a high prevalence of infectious diseases.

An essential requirement for assays based on nucleic acid amplification is protection from amplicon contamination, currently solved by working in specialized laboratories using dedicated spaces for sample preparation, amplification and detection. This approach is not applicable for field-testing, near-patient testing and in resource-limited settings.

SUMMARY OF INVENTION

The invention provides devices, a system, a method, and a machine according to the appended independent claims, to which reference should now be made. Preferred or advantageous features of the invention in its various embodiments and aspects are defined in dependent sub-claims.

Accordingly, in a first aspect the invention may provide a device for the processing of a sample comprising, a blister defined between first and second walls wherein the first wall is flexible such that the blister can be divided into one or more sealed regions by an external pressure applied to a portion of the first wall that urges the first wall towards the second wall. Preferably, the pressure is applied in the form of a two dimensional shape to form a sealed region in that shape.

It is preferable that the entire boundary or perimeter of at least one sealed region is formed by the external pressure.

The external pressure is preferably exerted by application of one or more shaped tools or platens to an outer surface of the portion of the first wall to urge it towards the second wall. At least one platen is preferably in the form of a two dimensional shape to form a sealed region having that shape.

Advantageously the platen may apply pressure corresponding to the perimeter or border of a two dimensional shape to form a sealed region having that shape.

The device may have first and second sealed regions having first and second perimeters, the regions being formed by application of pressure from first and second shaped platens, the first sealed region being enclosed within the perimeter of the second sealed region.

Shaped tools or platens may be actuated by a machine for automatic processing of the sample. Advantageously, this allows the sample to be processed within a single blister yet still undergo a complex processing protocol. The blister may, for example, contain a number of processing reagents retained at different locations within the blister. The blister can then be divided by the application of localised external pressure into one or more sealed regions, preferably with different sealed regions corresponding to the location of different processing reagents. The removal of the external pressure may result in the loss of a seal defining a sealable region. For example, a blister that has been divided by the application of one or more shaped platens into three separate sealed regions may revert to a single blister having a single internal space or cavity once the platens have all been removed.

It is preferable that, once a sample has been introduced into the blister, all further sample processing steps are carried out within the blister. This may reduce the chances of contamination of the sample by contaminating elements in the external environment. This may also reduce the risk that the external environment, for example, in the vicinity of a processing facility that uses the device, will be contaminated by the sample within the blister.

The device may be in the form of a card, cartridge or insert for introduction into a machine, for example into a port or docking station that places the device at a predetermined position in the machine, for automatically processing the sample according to predetermined processing steps. It is advantageous, therefore, that any object contained within the blister, for example an object for use in a processing step, is retained at a predetermined location within the blister. This may allow an automated processing means to be positioned in view of the predetermined location of the object.

Retaining an object at a location within the blister is particularly advantageous where the blister contains more than one object, particularly more than one different type of object. For example, the blister may contain more than one different type of processing reagent, each different type being located at a different predetermined location within the blister. An object may be a dried reagent or an object may be a sachet of liquid, for example a sachet containing a liquid processing reagent or a sachet containing a processing buffer. It is particularly advantageous that these different types of object can be retained at different predetermined locations within the blister even though the blister itself may define a single connected volume when delivered to a test site. Advantageously, a seal can be formed around a retained object by application of pressure from a shaped platen thereby forming a sealed region containing the object.

A device according this first aspect of the invention is, advantageously simple in structure and therefore easy to produce. Many prior art devices for processing samples involve complex patterns of channels and chambers to form complex flow paths. These devices need to be manufactured with these complex patterns defined by permanent seals, which may increase the cost of each device.

In the device of the present invention one or more sealed regions are formed within the blister during processing. Therefore, these sealed regions do not need to be formed during manufacture of the device and the device as produced has a simpler structure.

Some prior art devices make use of temporary, or frangible seals to isolate different sealed chambers. Generally, pressure is applied to break such a seal and allow communication between two different regions of the device. Breaking such frangible seals may be unreliable, however, particularly when the regions they separate only contain low volumes of material, for example 50 microliters or less of a liquid sample.

The use of an external pressure to form a seal as in the present invention advantageously overcomes the problem of unreliable frangible seals. As the pressure is applied a seal can be formed and this seal is removed when the external pressure is removed.

The use of an external pressure to form the entire boundary or perimeter of a sealed region has a further advantage. If a sealed region is formed from a combination of permanent seals and pressure seals (as may happen, for example, if a channel defined by a permanent weld or heat seal is closed by an external pressure across the channel) the integrity of the seal may be low. The applicants have discovered that when placing a pressure seal over a blister or channel a capillary fluid path may remain at the interface between the pressure seal and the heat seal. Even when this capillary flow path only allows a small volume of liquid to pass, the seal is compromised. One deleterious effect that may occur when a small amount of liquid is leaked is the unwanted re-hydration of reagents held in adjacent sealed regions. The applicants have found that the use of a pressure seal to form the entire boundary of a sealed region within the blister eliminates this problem.

In a second aspect the invention provides a device for processing a sample comprising a blister defined by, or between, first and second walls, in which an object is retained at a predetermined location within the blister. The blister defines a space that is sealed from the external environment, within which at least some of the processing steps for processing the sample may be performed. The object is for use in at least one of the processing steps.

In a third aspect the invention may provide a device for the processing of a sample comprising a blister defined between first and second walls in which the blister contains both solid and liquid objects, or processing reagents. The blister (as in all aspects of the invention) may provide a processing space that is sealed from the external environment and the blister may, therefore, contain reagents such as freeze dried or lyophilised reagents and liquid reagents or buffers. Preferably the liquid processing reagents or buffers are contained in one or more sachets and preferably all of the reagents are retained at predetermined locations within the blister.

Many sample processing protocols involve liquid reagents (in this context for brevity the term reagent is taken to include substances such as buffers or solvents that may be required during processing steps). The existence of both solid and liquid processing reagents within a single blister that is sealed from the environment reduces the number of elements that need to be introduced to the blister on site (i.e. only the sample, or a pre-processed sample, may need to be introduced). This further reduces the chances of contamination during or resulting from processing the sample.

In a fourth aspect the invention may provide a device for the processing of a sample comprising a blister defined between first and second walls wherein the blister contains a sachet of liquid, the sachet having a frangible or breakable seal that allows its liquid to be released into the blister on the application of a localised external pressure to the sachet. The term sachet may include any suitable liquid container that retains the liquid contents and releases them when the sachet is broken open or bursts on the application of a predetermined pressure or force. It is advantageous to perform the processing of a sample within a single blister that is sealed from the external environment. In many processing devices where sealing from the environment is an important issue, ways must be found to introduce liquid processing reagents where these are required for a particular processing protocol. By including a sachet containing the liquid within a sealed processing blister the risks of contamination when introducing a liquid reagent are reduced. Furthermore, assembly or production of the device may be made much easier as a sachet of liquid is a discrete, tangible and dry object. Thus, a sachet may be considerably easier to handle during assembly than, say, a volume of liquid that has to be loaded into a processing device without having its own containment. This advantage is particularly clear when it is borne in mind that the device needs to be assembled in very clean, sterile conditions.

Preferably, a wall of the blister is flexible such that the liquid within the sachet may be deployed by the application of an external pressure to the sachet through the flexible wall. Thus, the liquid within the sachet may be retained within the sachet, and therefore away from the sample and any processing steps being carried out within the blister, until the liquid is required.

In a fifth aspect the invention may provide a device for the processing of a sample comprising a blister defined between first and second walls and having a vacuum port that allows air or gas to be withdrawn from the blister.

A vacuum port may simply be a port sealed by a resilient septum, through which a syringe may be inserted as a means to apply a vacuum.

There may be a number of advantages to applying a vacuum to a blister for processing a sample. If the blister has a wall that is flexible, the withdrawal of air may create a vacuum within the blister and urge the first and second walls of the blister together. Advantageously, this may assist in retaining any objects placed within the blister at predetermined locations.

Where the blister can be divided during processing into one or more sealed regions, as described above, then a vacuum may aid in the transfer of the sample between these regions as the seals are removed. A vacuum may also in such circumstances aid mixing of the sample by creating turbulence when a region that is at atmospheric pressure is opened up by the removal of a seal to a region that is at a lower than atmospheric pressure.

Removal of air may also be important for performing processing protocols that, for example, are more effectively performed in the absence of oxygen and/or humidity.

In its broadest sense the invention provides a device for processing of a sample comprising a blister or sealed enclosure defined by or between first and second walls. The various different characterising features defining aspects of the invention as described above may exist in any permutation or combination within a single device according to the invention. The following preferred features relate to a device according to any aspect described herein.

Preferably the first wall of the blister is flexible such that a localised external pressure urging a portion of the first wall towards the second wall can produce a localised seal. This may allow the blister to be divided during processing into two or more temporarily sealed regions for carrying out different processing steps. Preferably the seal opens when the localised external pressure is removed. Advantageously, such seals may be formed and opened multiple times if required for a particular processing protocol.

It may be advantageous that an object is retained at a predetermined location within the blister. Thus, when manufacturing a device that includes an object for use in processing of a sample, such as a dried reagent or a sachet of liquid, such objects can be placed within the blister on manufacture. One method of locating an object has already been mentioned above, i.e. the application of a vacuum to the blister to draw in a wall of the blister against the object, thereby retaining the object at a predetermined location within the blister.

An object, such as a dried reagent or a sachet of liquid, may be retained at a location within the blister by mechanical locating means, such as dimples or recesses defined in the first wall or the second wall of the blister, or in any other appropriate manner. Location of objects within the blister is particularly preferable where the processing of the sample involves forming the blister into more than one temporarily sealed chamber by the application of external pressure, as the boundaries between the chambers may then be positioned so that the objects are positioned in desired chambers.

Preferably the device comprises a sample introduction port to allow the introduction of a sample into the blister. The port could be a port extending through the first wall or the second wall of the blister or could be a port that extends into the blister at a join between the two walls. Such a sample introduction port may comprise a resilient septum that allows introduction of a sample using a hypodermic needle.

The blister may be defined by or between a first wall that is a flexible film and a second wall that is a substantially rigid base plate, the flexible film being joined to the base plate to form a blister. The use of a base plate may be advantageous where the device is a card or cartridge for introduction into an automatic processing machine. The base plate may provide support for the blister, particularly where the blister is to be subjected to external pressures.

Both first and second walls may be a flexible film. In this situation the device may further comprise a frame to support the second wall.

The device may comprise a gasket disposed within the blister. Where there is a gasket, localised pressure urging a portion of the first wall towards the second wall may sandwich the gasket between the first wall and second wall to form a localised seal. Preferably the gasket is a material that is disposed on the first or second wall within the blister to define one or more sealable regions within the blister.

Where the second wall of the blister is a base plate it is preferable that any gasket material be a material softer than the base plate that is disposed on the base plate within the blister.

The gasket may define locating dimples or recesses.

As the first wall is flexible and the device may contain reagents, it may be advantageous that the device includes a cover for protecting the device during transit or during handling. Such a cover may be removable or may be hinged, for example to a base plate of the device if a base plate is present. Any cover may be simply removable to allow a sample to be processed using the device. Alternatively the cover may retract or open on placing the device into a processing machine.

A cover for a device according to an aspect of the invention may comprise structures such as ribs that exert an external pressure to a portion or portions of the first wall, when the cover is closed over the device, to form temporarily partitions or sealed regions within the blister. These partitions or regions may advantageously help to maintain objects such as reagents in predetermined positions within the blister during transportation and storage. This may be of particular advantage where an object, such as a freeze-dried reagent, becomes damaged or fragmented during transit. The use of a cover shaped to partition or seal regions of the blister containing objects allows all fragments of a damaged object to be maintained in a predetermined location such that a valid processing may still be carried out (i.e. the volume of a reagent in a predetermined location is not diminished due to fragmented portions migrating to a different region of the blister.)

Preferably the blister can be divided into one or more sealed regions by application of one or more shaped platens to urge one or more portions of the first wall towards the second wall. This allows the temporary formation of more than one sealed chamber within the sealed blister thereby allowing complex processing protocols to take place within a single blister. Particularly preferably the sealed regions can be sealed and unsealed sequentially to allow the sample and/or reagents within the blister to pass between the regions in a predetermined manner. For example, one or more of the sealed regions may contain a processing reagent or more than one processing reagents and removal of the seals forming the sealed regions may allow the sample to contact the processing reagent or reagents, either by movement of the sample towards the reagent or by movement of the reagent towards the sample.

Preferably, the sample can be mixed by exerting an oscillating external pressure to the blister. For example, a plunger or plurality of platens or plungers may be actuated against the first wall of the blister thereby repeatedly displacing the sample contained within the blister and causing its mixing. Similarly, the sample may be moved to different regions within the blister by the application of pressure to the blister that effectively squeezes the sample to different regions of the blister. This may be advantageous where a liquid sample is required to be moved to a different portion of the blister.

Advantageously a device according to the invention may further comprise an analysis means. It may be important that the sample is not removed from the device, even after processing, as this may contaminate the environment in the vicinity of the processing station using the device. In such a case it is particularly advantageous to have an analysis means located within the device. Such an analysis means could be located within a temporary sealable region of the blister or it could be located in a separate analysis chamber that is in communication with the blister, for example via an exit port from the blister.

Preferably the analysis means is a test strip that contacts the sample and produces a visual result. Thus, it is preferable that the analysis means is located in a portion of the device that is at least in part transparent such that the analysis can be determined optically or visually.

The invention may have particular application to a device for the processing of a biological sample and particularly to a device for the amplification and detection of nucleic acid in a biological sample. The device could, however, be used for processing other samples, for instance environmental or chemical samples.

The invention may also provide a machine for automatically processing the sample in a device according to any aspect described above. The machine comprises a bay or slot for receiving the device and a tool or platen for applying a localised external pressure to the device when loaded in the machine. Preferably the machine has a plurality of tools or platens adapted to interact with the device, and is computer-controlled to operate the tools or platens so that a predetermined sample processing protocol can be reliably and repeatably performed.

As many processing protocols involve incubation steps it may be advantageous for the machine to further comprise a heater for applying heat to a device. Particularly advantageously the heater may be part of a tool or platen for interacting with the blister of the device. As an alternative, a portion of the bay or chamber for receiving the device or the entire bay for receiving the device may be heated and, thus, able to act as an incubator. It may be advantageous for the bay to act as an incubator and for one or more platens to be heated. This combination may allow the temperature of the sample to be controlled within fine tolerances.

Processing protocols may also require cooling stages or steps or the temperature may need to be swiftly lowered in a particular protocol and, consequently, a cooler may be provided. Advantageously, a tool or platen for interacting with the blister may be cooled, for example by a compressible gas, or may comprise a cooling means. For example, a tool or platen may have cooling channels for removing heat from the blister via a cooling liquid or a cooling gas to lower the temperature of the cooled sample, or a tool or platen may comprise a thermoelectric cooling means, for example a Peltier cooler. Where cooling is required, the bay or chamber may also be cooled as an alternative to or in addition to cooling of platens.

The machine may comprise an actuatable platen that is substantially tube shaped. Such a platen may be able to provide a two dimensional seal to a portion of the blister. Advantageously, the machine may comprise a further platen independently actuatable within the tube shaped platen for forming further sealed regions within an outer sealed region or for applying an oscillating interaction for mixing a sample.

In a further aspect of the invention a system is provided for processing a sample comprising a device as described above and a machine for receiving and manipulating the device. The machine comprises a platen for applying pressure to the first wall of the device to create a seal.

Preferably the system includes a machine having one or more platens that can be independently operated to close and open seals in a predetermined sequence.

The invention may also provide a method of processing a sample in a device having a blister formed between a first wall and a second wall. In a preferred method the first wall is flexible and the method comprises the steps of applying a localised external pressure to urge a portion of the first wall towards the second wall to form first and second sealed regions within the blister, introducing a liquid sample to the first sealed region, and removing the localised pressure to open the seal between the first and second sealed regions.

Preferably the blister is preloaded with dried reagents held at predetermined locations and the external pressure is applied such that a first reagent is located in the first sealed region and a second reagent is located in the second sealed region. For example, the localised external pressure may form a seal that separates a region of the blister in which a first reagent is located and a region of the blister in which a second reagent is located, the two reagents then being in two temporarily sealed regions within the device. Blisters may hold more than one reagent, depending on the processing protocol required.

Typical processing steps such as incubation, heating or mixing may occur in the first sealed region before opening the seal between the first and second sealed regions. Likewise, where there are more than two sealed regions formed in the device, processing steps that are typical for processing a sample may be performed in each region prior to opening a seal and allowing communication of that region with the next sealed region. Typically, each sealed region will contain a processing reagent, or will isolate an entry or an exit port, if present.

A preferred method of applying the localised external pressure is to use a shaped platen or tool that is actuated by a machine. The shaped platen may be shaped to apply a pressure across the width of the blister thereby dividing it by forming a seal across the blister's width. Preferably the platen will apply a pressure in the form of a two-dimensional shape, for example a circle, to the blister to form a sealed region in that shape, i.e. a sealed region with a boundary or perimeter having that two-dimensional shape. It may be possible to form sealed regions within other sealed regions by the application of platens that are located inside other, hollow or tubular, platens. For example the platens may be a series of concentric tubes that apply pressure in a series of concentric circles to the blister, thereby producing a first sealed region that is entirely located within a second sealed region.

Preferably more than two sealed regions are formable within the blister as this allows more reagents to be individually located and more complex processing protocols to be applied to the sample. A plurality of tools or platens can be used to apply external pressure to form more than two sealed regions within the blister and preferably the seals separating each of the more than two sealed regions can be opened in sequence to allow the liquid sample to communicate with each region in predetermined order.

The method may include a mixing step and mixing may be advantageously carried out by oscillation of the tool or platen against the first wall of the blister. Many processing protocols call for the use of liquid buffers or reagents and preferably the device contains a liquid buffer or reagent contained in a sachet located within the blister. Preferably the liquid is releasable by the application of an external pressure to the sachet. The sachet may, therefore, have a frangible seal that is breakable upon a predetermined external pressure being applied.

The method may call for the movement of the sample within the blister, for example to contact different processing reagents or to move the sample out of the blister through an exit port. Preferably the movement within the blister is achieved by application of external pressure from tools or platens.

The method is particularly applicable to performing a protocol on a sample suitable for amplification of a nucleic acid.

Preferably, the method includes a further step of analysing the sample. Such analysis is preferably done after processing has been completed. A preferred analysis method is to contact the processed sample with a test strip that is located within the device, for example located within a separate analysis chamber that is in communication with the blister. An exit port allowing communication between the blister and an analysis chamber may be isolated with a seal formed by the action of a tool or platen until the sample is processed and the seal protecting the exit port is removed.

It may be advantageous to measure or select a predetermined volume of liquid, for example to pass into an analysis chamber for analysis. Some processing or analysis steps may require that a defined volume of liquid, for example a defined volume between 100 and 500 microliters, be used. Thus, the device may comprise a suitable means, or the method of using the device may comprise a suitable method step, for measuring or selecting such a volume of liquid for further processing or for analysis.

A preferred means of selecting a predetermined volume of liquid is to apply an external pressure to a portion of the blister containing the liquid sample, to form a seal that subdivides that portion of the blister and separates out the predetermined volume of liquid on one side of the seal. The separated volume can then be passed to another region of the blister or into an analysis chamber.

For example, this method may be used to select a predetermined volume of a sample for processing. A larger volume of the sample may be introduced, for example by injection from a syringe through a septum, to fill a metering portion of the blister that is preferably of elongate shape and bounded at one end by a first seal formed by an external pressure. Once the metering portion of the blister is filled, a second seal is formed, by application of an external pressure, at a predetermined distance from the first seal. The desired predetermined volume of the sample for processing is thus isolated within the portion of the blister between the first and second seals. The first seal can then be released to allow the predetermined sample volume to flow into a further portion of the blister for processing and analysis.

The method may also comprise a step of disposing of the device. It may be important that the processed sample is not allowed to contaminate the region around the test site so it may also be important that the used device is processed with an appropriate decontamination procedure prior to disposal.

Where the processing protocol involves amplification and detection of nucleic acid it may be advantageous to perform a treatment to neutralise previous processing reactions or to deactivate amplified products to prevent priming of a new amplification reaction. It may, thus, be advantageous to treat the device (for example a device according to any embodiment or aspect described herein) and the used sample post-analysis to help prevent contamination of the point of use site. For example, to help prevent amplicon carry over contamination, the amplicon left in the device after a detection step could be treated with nucleic acid modifying or hydrolysing agents that prevent priming of further amplification reactions. Decontamination may be particularly desirable where batches of samples are to be tested on the same site.

One such decontamination treatment described in U.S. Pat. No. 5,035,996 involves incorporation into the amplified product of a ribo- or deoxy-nucleoside triphosphate (rNTP or dNTP) base that is not generally found in the sample to be analysed, for example dUTP in the case of DNA analysis. The amplified product will thus have a sequence that has uracil in multiple positions. The enzyme uracil DNA glycosylase (UDG) is added to the sample prior to amplification. This will cause enzyme hydrolysis of any contaminating reaction product (containing uracil) without affecting the natural DNA in the sample.

Preferably decontamination is a chemical treatment or reagent that not only modifies, but also degrades nucleic acid e.g. non-enzymatic degradation of nucleic acid with chemical nucleases. Examples of chemical nucleases are known in the art, e.g. divalent metal chelate complexes, such as copper phenantroline—Cu(II) or Ascorbate—Cu(II) cleavage as described by Sigman D. S et al (J Bio Chem (1979) 254, 12262-12282) and Chiou S. (J Biochem (1984) 96, 1307-1310).

A decontamination reagent could be conveniently delivered into the blister of the device after analysis of the sample for example by injection through the sample introduction port. The device may, alternatively, be preloaded with both processing reagents and a post-analysis treatment or decontaminating reagent.

DESCRIPTION OF SPECIFIC EMBODIMENTS

Embodiments of the invention will now be described by way of example with reference to the accompanying drawings in which:

FIG. 12 illustrates the removal of a seal around an exit port allowing the processed sample to contact an assay strip.

Figure 1:
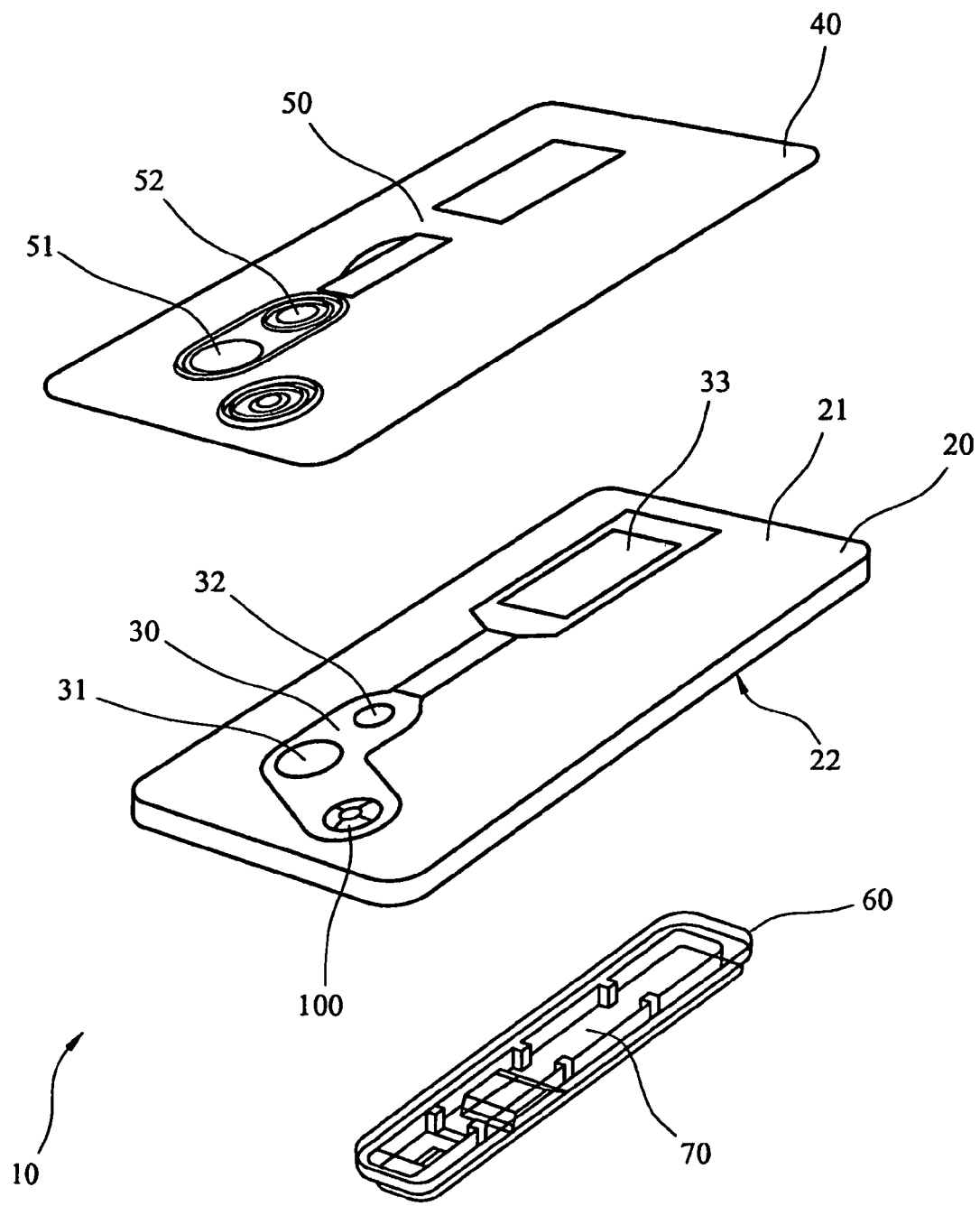
FIG. 1 is an exploded view of a device according to an embodiment of the invention.

FIG. 1 is an exploded view of a device embodying aspects of the invention. The device 10 comprises a base moulding or base plate 20 having a first side 21 and a second side 22 (not visible in FIG. 1). The base moulding is made of polypropylene but could be made of any suitable material, for example any substantially rigid polymer. A gasket 30 is fixed or formed, for example by overmoulding, on the first face 21 of the base plate. The gasket is made of a softer, more rubber like, polymer material than polypropylene, for instance, a thermoplastic elastomer (TPE) such as Dryflex® manufactured by VTC TPE Group or similar materials manufactured by companies such as Kraiberg or Plastic Technology Service Limited (PTS). The gasket is formed with depressions (31, 32 & 33) in order to locate objects within the device. The device further comprises a flexible film 40 that is attached to the first face of the base moulding and forms a blister 50 having the flexible film as a first wall and the base plate as a second wall. The blister 50 is formed with the gasket 30 substantially disposed inside the blister. The flexible film may be any suitable film, for example a thermoformed film having predetermined moisture and vapour barrier properties. A preferred example of a suitable film is Aclar®. Aclar® is a trade name for polychlorotrifluoroethylene (PCTFE).

A further example of a suitable film material is a polypropylene (PP) based flexible film such a TEKNIFLEX® MED 3014-0080. Such PP films may not have the moisture protection properties as specialist films such as Aclar® but may stretch and seal more effectively and be cheaper. Any reduction in moisture protection provided by a flexible film can be overcome by sealing the device in a foil bag for transport and storage.

The flexible film has thermoformed dimples to locate objects within the blister.

The device further comprises an assay cover 60 that is fixed to the rear face of the plate and defines an assay chamber or analysis chamber 70. Both the interiors of the blister 50 and the assay chamber 70 are thus sealed from the external environment. An exit port 100 defined through the base plate provides communication between the blister and the assay chamber.

The blister 50 has a plurality of location points defined by depressions in the gasket and corresponding dimples in the flexible film for locating reagents within the blister (for example at 51 & 52). The dimples prevent the reagents from substantially shifting position within the blister, which at this stage is a single chamber.

Figure 2:
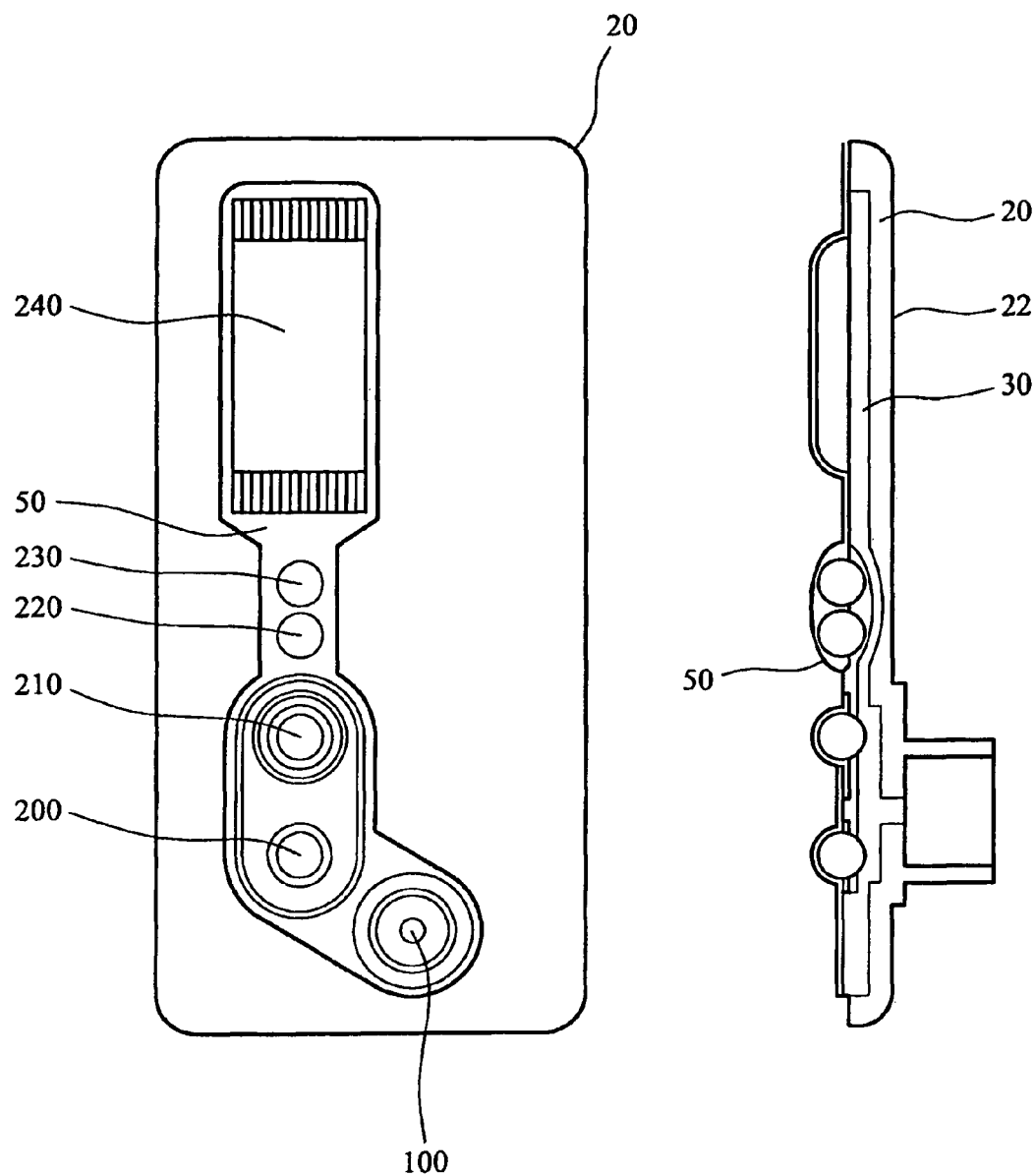
FIG. 2 is a view of the device of FIG. 1 from the front and from the side showing the location of various reagents and ports.

FIG. 2 shows front and side projections of the device and illustrates the locations within the device of a first freeze-dried reagent 200, a second freeze-dried reagent 210, a third freeze-dried reagent 220, a fourth freeze-dried reagent 230 and a liquid detection buffer contained within a sachet 240. The freeze-dried reagents and the sachet of liquid are located in the device during its manufacture and prior to the blister 50 being sealed. This advantageously avoids the need for handling of reagents on site where sample processing is to be performed or the need to open the device on site, and may thus reduce the potential for contamination.

Figure 3:
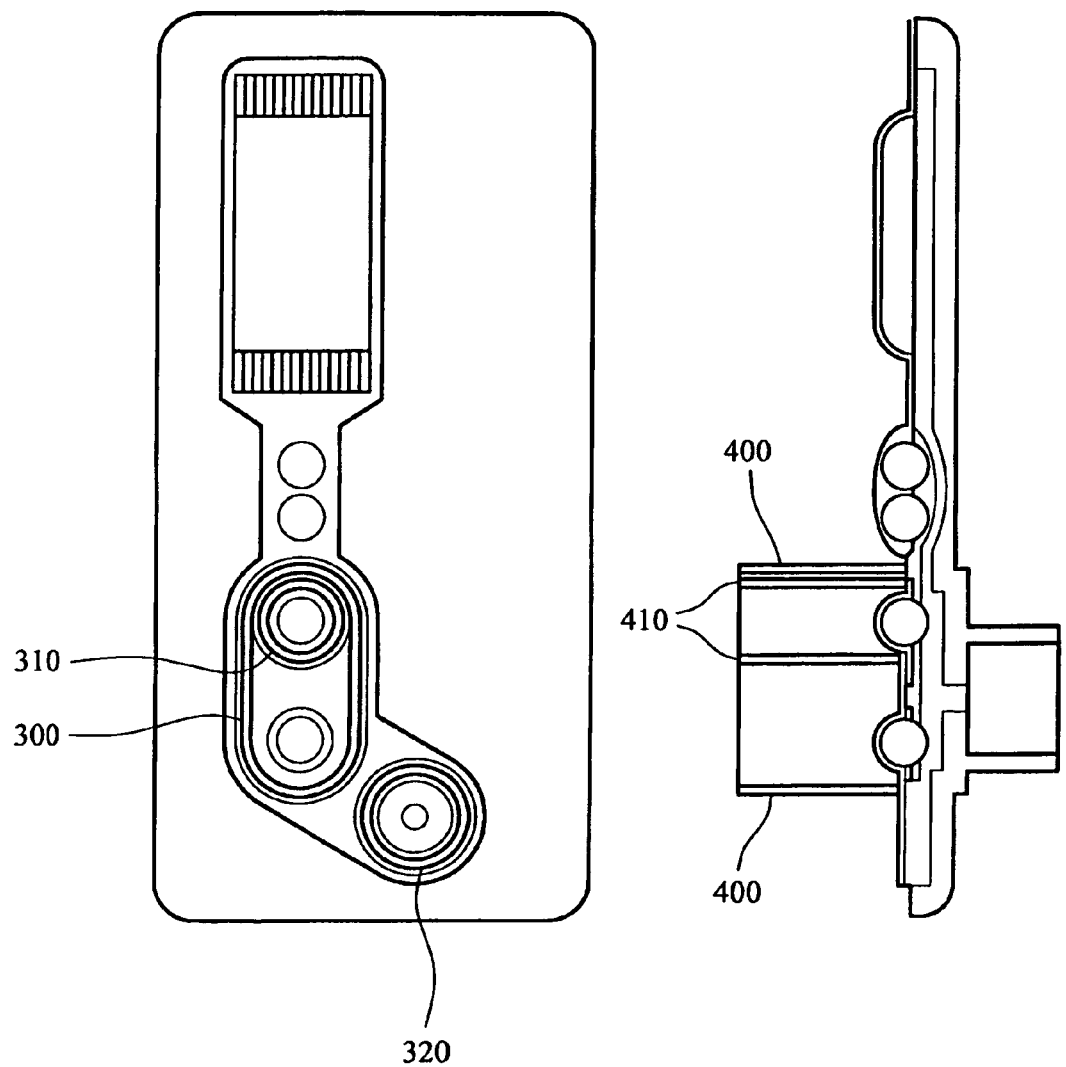
FIG. 3 is a view of the device of FIG. 1 from the front and from the side, the side view showing the device as loaded into a machine with pressure seals being formed by tubular platens

As the film is flexible it is possible to apply an external pressure urging a portion of the film towards the base plate and against the gasket material thereby forming a localised seal. FIG. 3 shows front and side projections of the device and illustrates the position of three separate seals for producing sealed is regions within the blister during the processing of a sample. The seal positions shown are an outer seal 300 that bounds the first and second freeze-dried reagents, an inner seal 310 that bounds the second freeze-dried reagent thereby separating it from the first freeze-dried reagent within the outer seal and an outlet seal 320 that provides a seal around the exit port leading to the assay chamber.

The side view of FIG. 3 illustrates the device when loaded into a machine and also illustrates the use of two platens, first platen 400 and second platen 410, to create the inner and outer seal. Both first platen 400 and second platen 410 are substantially tubular and separately actuatable with second platen 410 being actuatable within the bore of the first platen 400.

Figure 4:
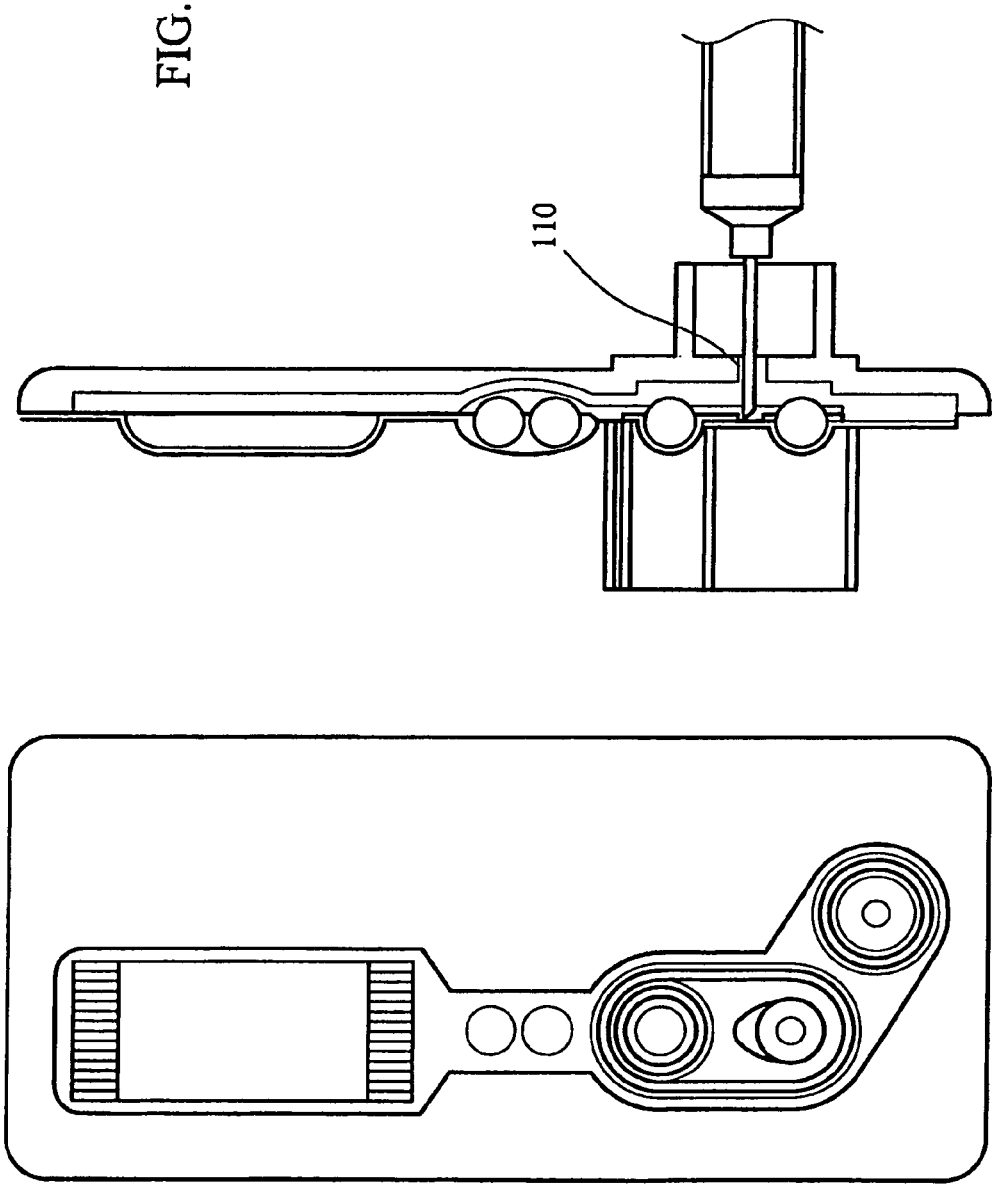
FIG. 4 shows a front view and a side view of a sample being introduced into a device according to FIG. 1.
Figure 5:
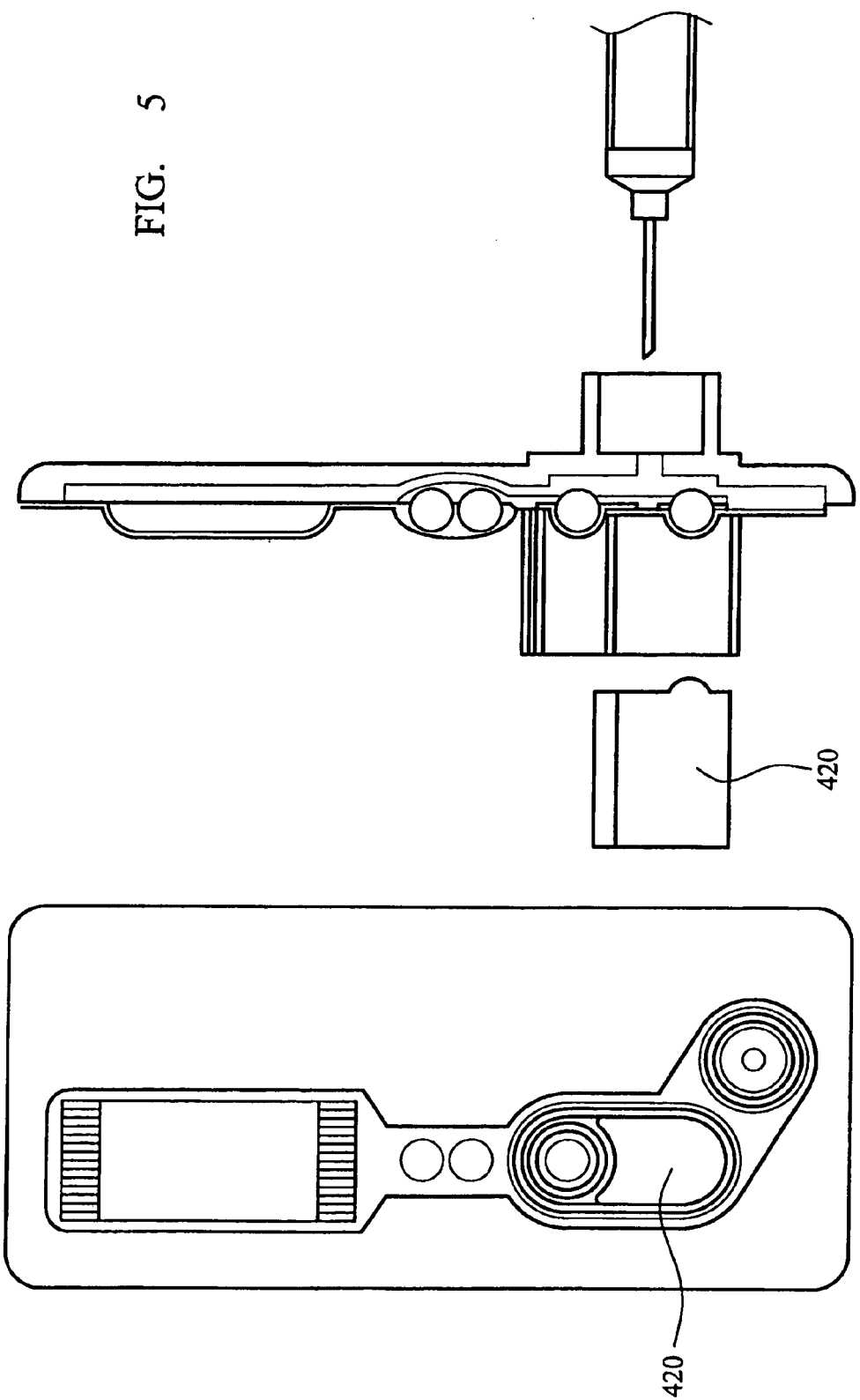
FIG. 5 illustrates the introduction of a mixing/heating platen.
Figure 6:
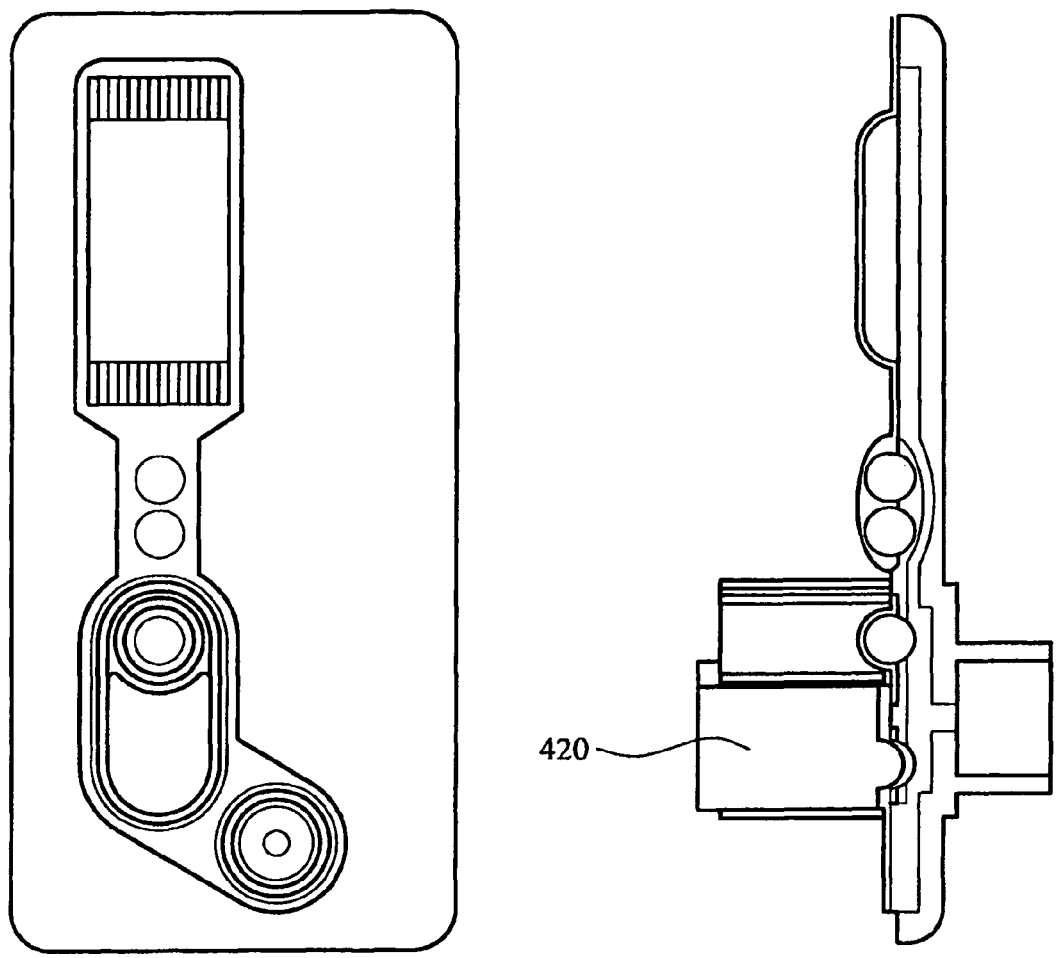
FIG. 6 illustrates the use of a mixing platen.
Figure 7:
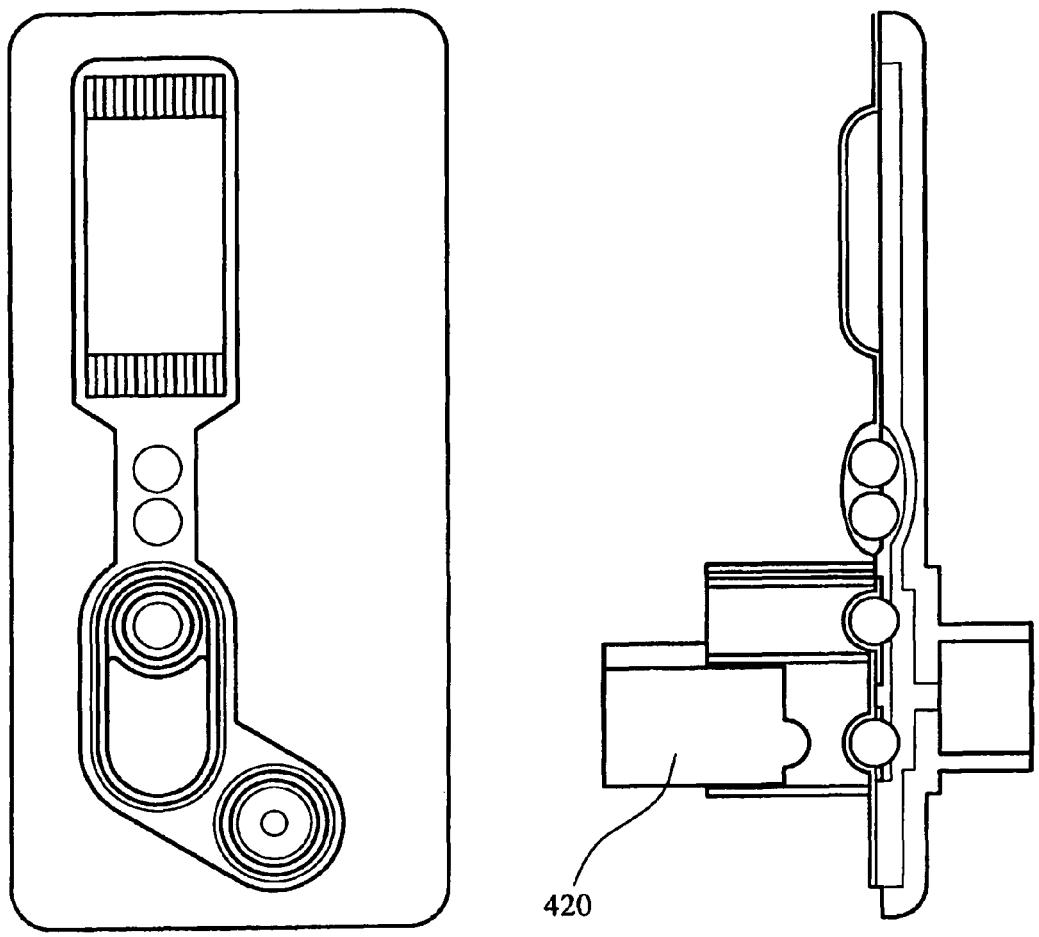
FIG. 7 illustrates the use of a mixing platen.
Figure 8:
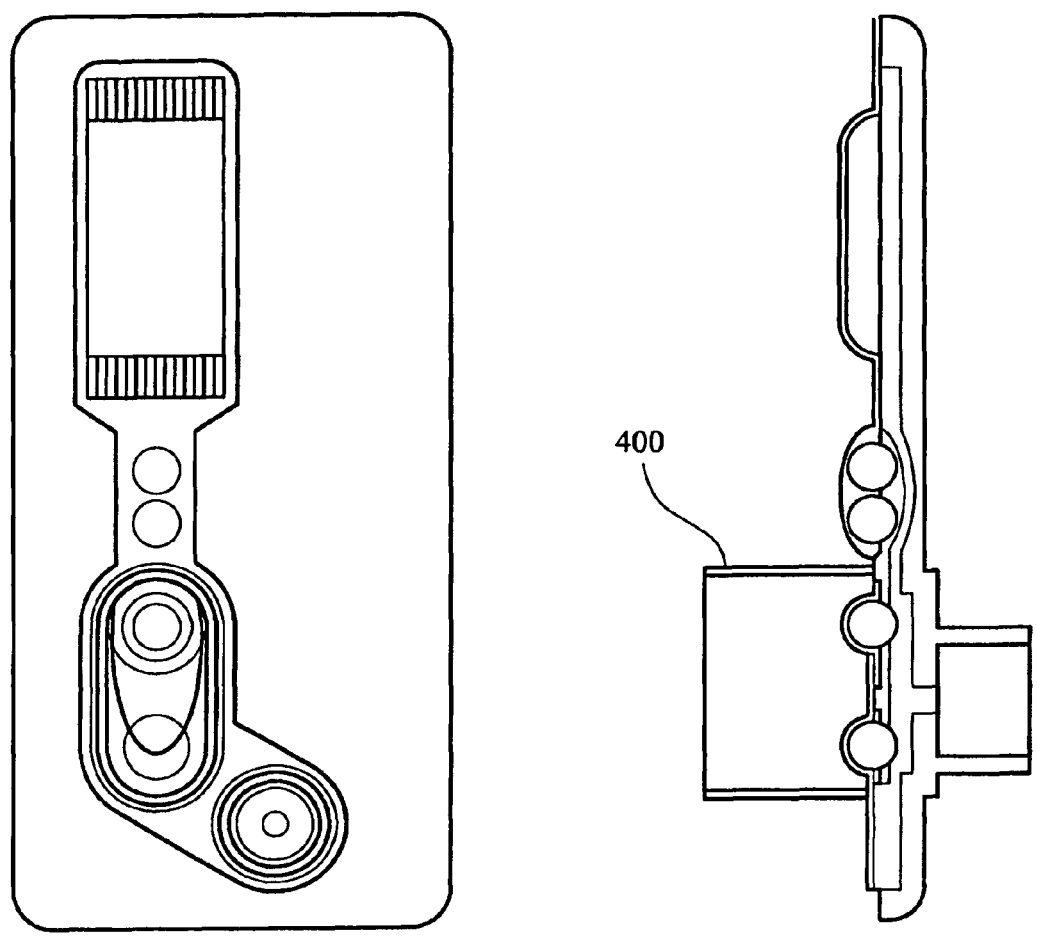
FIG. 8 illustrates the removal of a platen to allow the sample to communicate with a second reagent.
Figure 9:
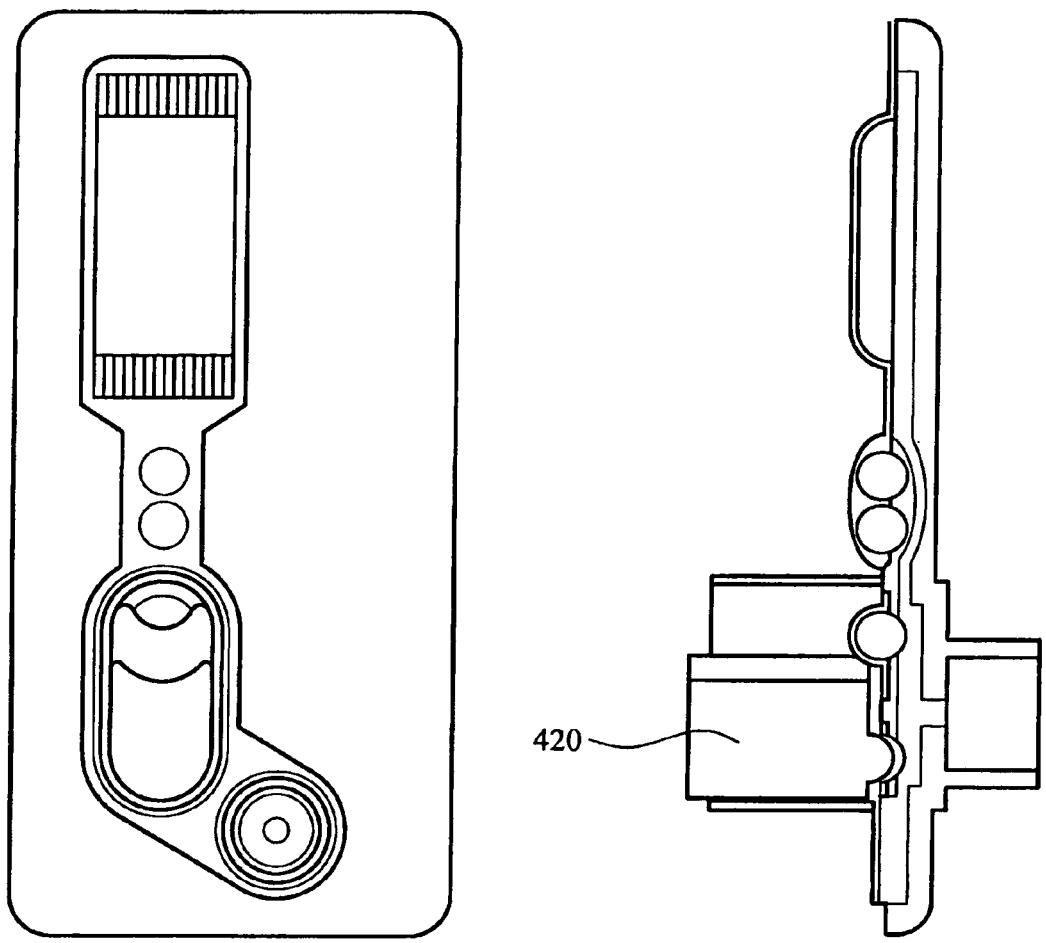
FIG. 9 illustrates the use of a platen to move the sample towards the second reagent.
Figure 10:
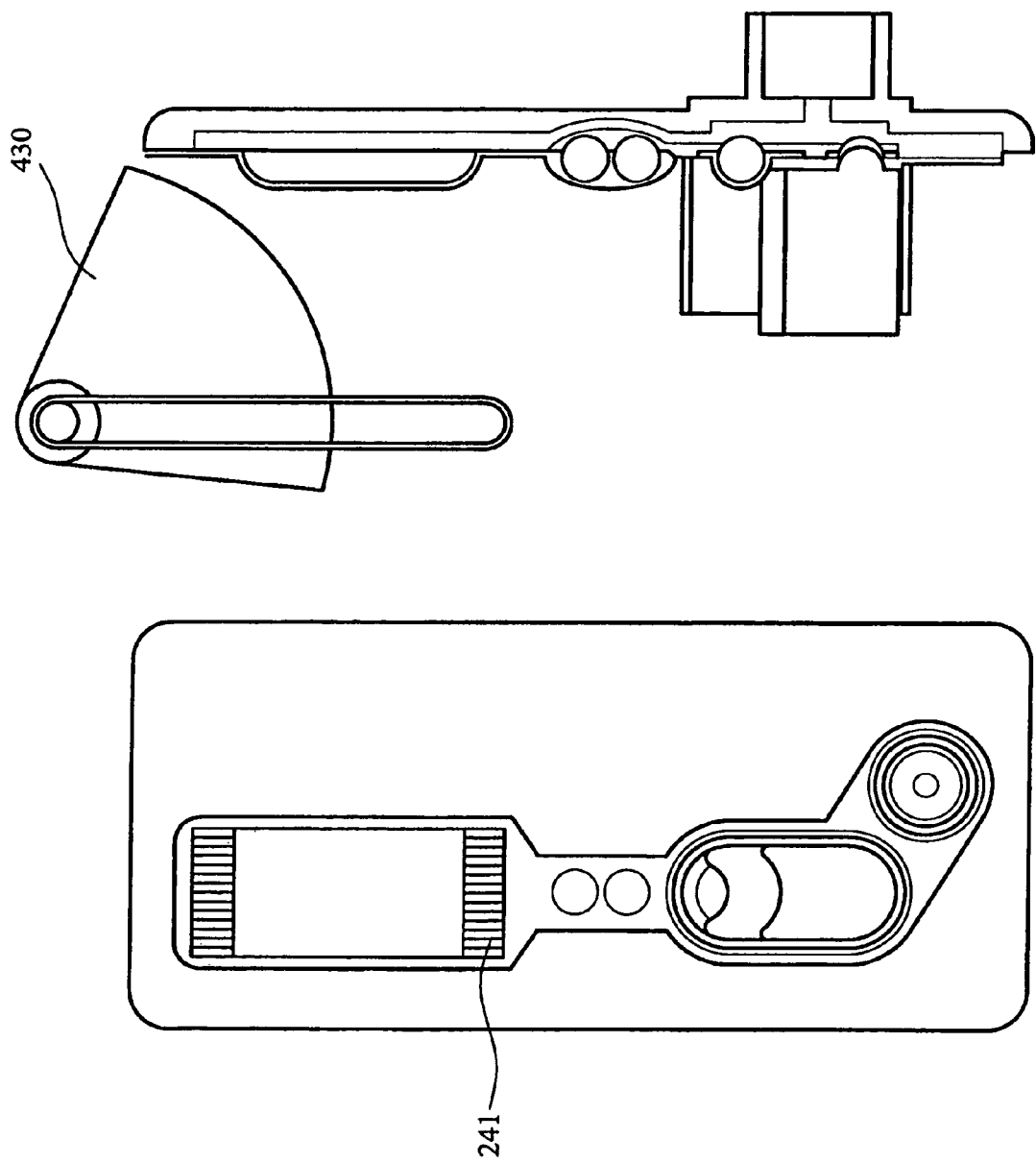
FIG. 10 and FIG. 11 illustrate the use of a roller element to liberate liquid from a sachet.
Figure 11:
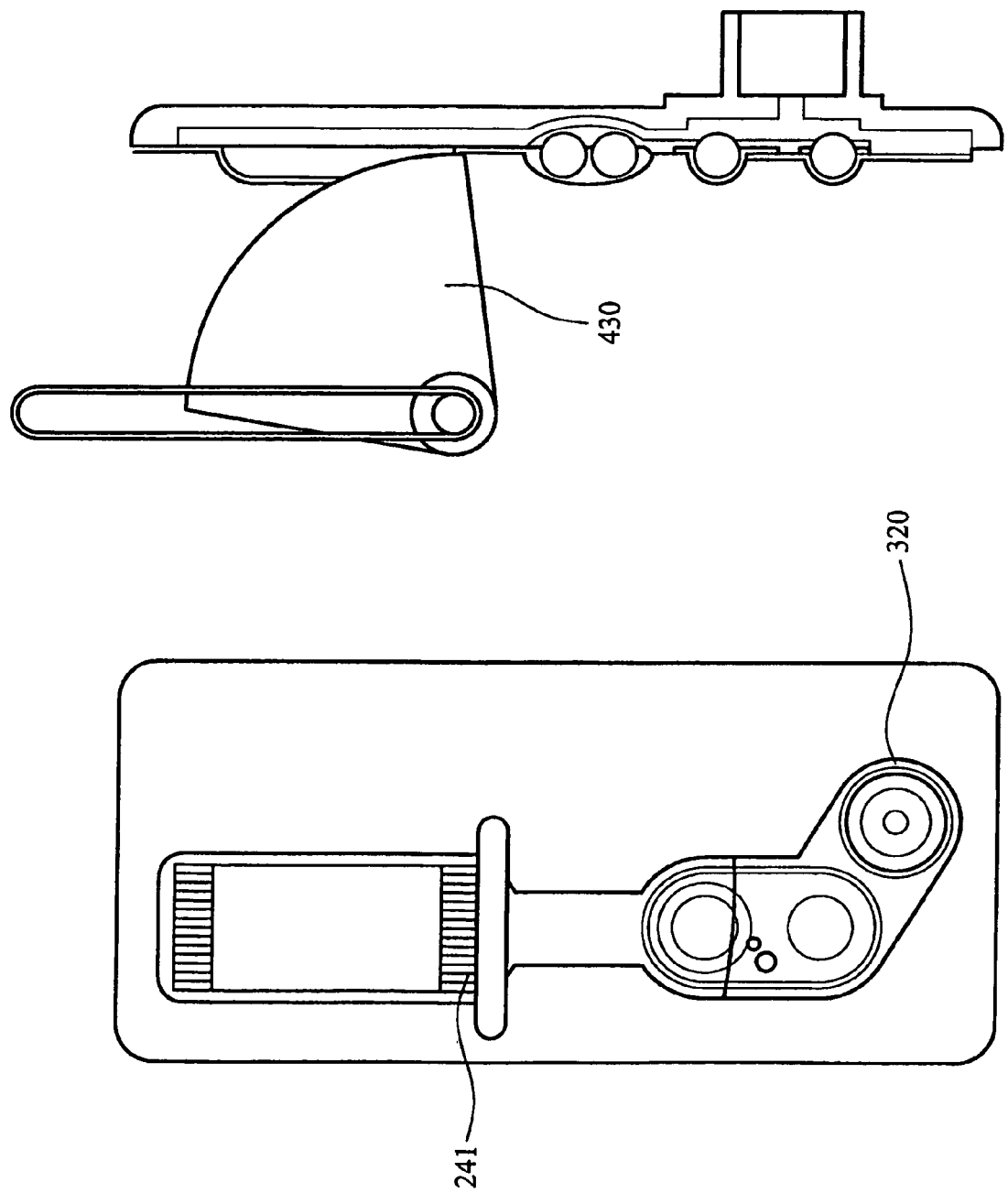

The following steps describe the use of the device to perform a nucleic acid amplification and detection protocol.
Step 1; The device is loaded into a machine in a vertical direction for the automatic processing of a sample as shown in the Figures and the seals (300, 310, 320) are applied to the blister by application of external forces by a plurality of platens (400, 410, third platen not shown). See FIG. 3.
Step 2; A sample is introduced into the blister via an access port 110 defined through the base plate; see FIG. 4. The access port may comprise a rubber septum and a syringe may therefore be used to introduce the sample.
Step 3; The liquid sample contacts and reacts with the first reagent 200 (see FIG. 4). The mixture comprising the liquid sample and the first reagent is prevented from accessing the third and fourth freeze-dried reagents by the seal formed by pressure exerted by the first platen 400, and from communicating with the second freeze-dried reagent by the seal formed by pressure exerted by the second platen 410.
Step 4; A mixing and heating platen or plunger 420 is introduced through the bore or lumen of the first platen as illustrated in FIG. 5. Mixing may be effected by oscillation of the mixing/heating platen 420 as shown in FIGS. 6 and 7.
Step 5; The mixing/heating platen 420 is held over the blister in contact with the film in order to perform a heating and incubation step of the processing protocol.
Step 6; After appropriate mixing, heating and incubation has been performed on the sample, the second platen 410 is removed allowing the sample to contact the second freeze-dried reagent; see FIG. 8.
Step 7; In order to force the liquid sample to contact the second freeze-dried reagent, the mixing/heating platen 420 is reintroduced and squeezes the liquid sample into the region of the blister occupied by the second freeze-dried reagent. (FIG. 9). Mixing may again occur by oscillation of the mixing/heating platen.
Step 8; A cam or roller 430 is applied to the blister in the region in which the sachet is located; see FIGS. 10 and 11. The cam or roller causes a pressure to build against a frangible end of the sachet 241, causing the liquid to be liberated into the blister where it reacts with the second and third freeze-dried reagents. This liberating pressure may alternatively be applied by a reciprocating platen or plunger acting to apply pressure to the sachet.
Step 9; The first platen is removed to allow the sample to contact liquid liberated from the sachet. This is illustrated in FIG. 11.
Step 10; After any further mixing or processing (for example incubation) has occurred to produce a processed sample, the final seal 320 is removed to allow the processed sample to enter the assay chamber 70 where it contacts an assay strip 71; see FIG. 12, which shows front and rear projections of the device.
Step 11; The results of the test are visually shown by the assay strip through the assay cover.
Step 12; The device is removed from the machine and disposed of.

Figure 13A:
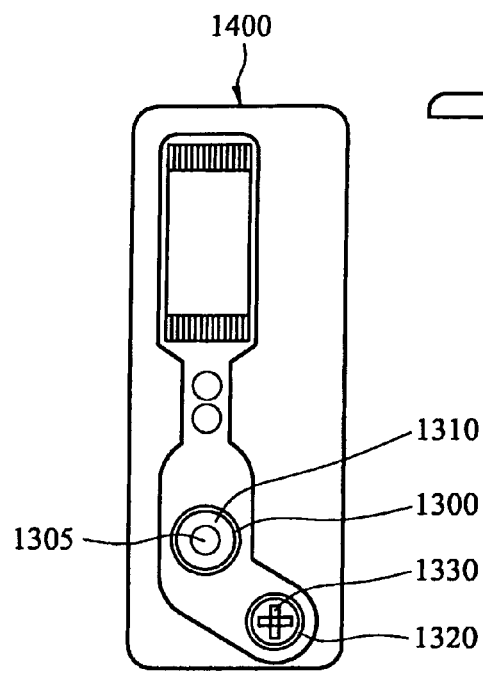
FIG. 13A illustrates a front view a device according to a second embodiment of the invention.

It should be clear that different protocols can be used in a device according to the invention. For example, either the first or the second dried reagent may be omitted and, therefore, only the inner seal or only the outer seal from the above example need be formed. If only one such seal is formed it could be circular, or oval, or any other suitable two-dimensional shape. FIG. 13A illustrates such a device in which only two pressure seals are formed, the first 1300 defines a first sealed region 1310 surrounding reagent 1305 within the device 1400, and the second 1320 forms a second sealed region 1330 surrounding an exit port.

Figure 13B:
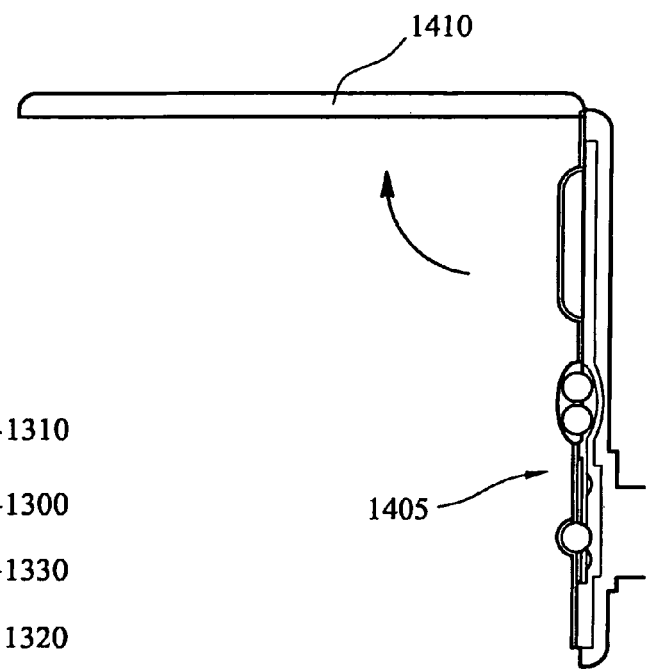
FIG. 13B illustrates a side view of a device according to the second embodiment of the invention.

FIG. 13B illustrates the device of FIG. 13A viewed from the side. This figure illustrates a hinged cover 1410 that protects the front face 1405 of the device during transit and handling. The hinged cover opens when the device is inserted into a processing machine.

Figure 14:
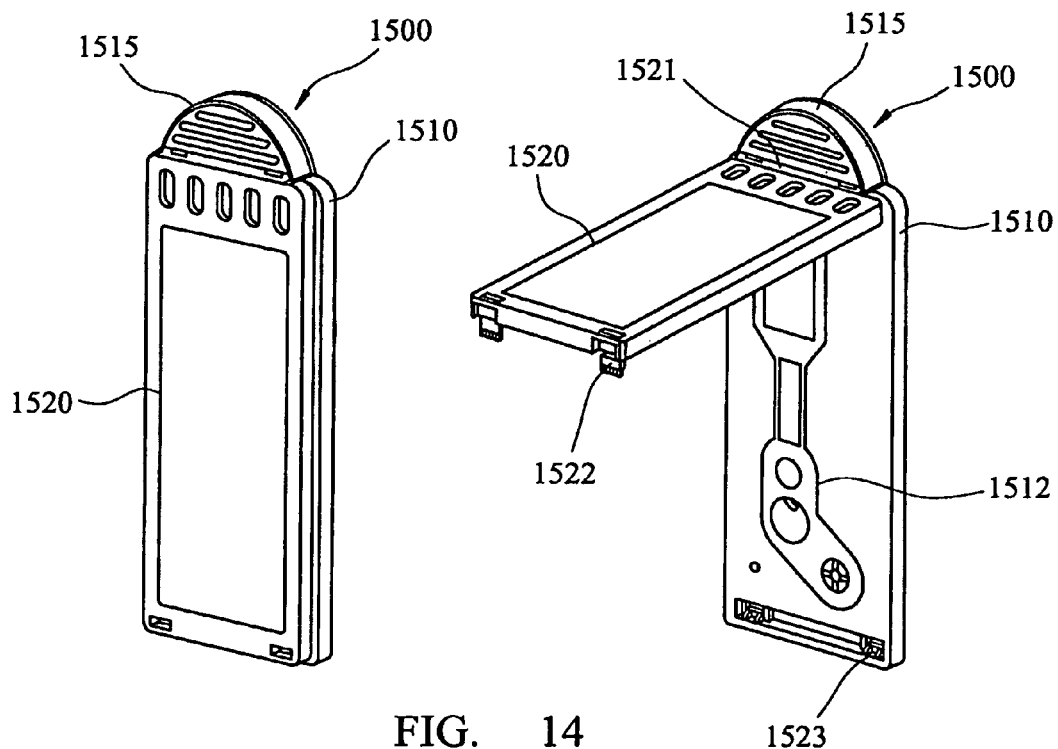
FIG. 14 illustrates perspective views of a device according to the invention.

FIG. 14 illustrates a further embodiment of a device according to the invention. The device 1500 has a solid base-plate 1510 incorporating a finger grip 1515 for facilitating handling. A blister 1512 containing reagents is formed on the base-plate from a flexible material. The blister is protected during transit and handling by a hinged cover 1520. The cover is connected to the base-plate at a hinge 1521 and is held in place by snap-fit connections 1522 that engage with corresponding features 1523 defined in the base-plate.

In a further embodiment of the invention the device may comprise a vacuum port for withdrawing air from the blister prior to processing the sample. The vacuum port may comprise a rubber septum spanning a hole in the base plate. If a vacuum is to be applied to a device it may be advantageous to select a film for forming a wall of the blister that has suitable barrier properties, for example a film that is substantially gas impermeable.

The invention claimed is:

1. A device for the processing of a sample comprising, a single blister only, the blister defined between first and second walls wherein the first wall is flexible such that the blister can be divided into one or more sealed chambers by an external pressure applied to a portion of the first wall that urges the first wall towards the second wall, the pressure being applied in the form of a two dimensional shape to form a sealed chamber in that shape, wherein the blister, once divided by operation of the external pressure, is operable to become undivided when the external pressure is released.

2. A device according to claim 1 in which the first wall is flexible such that a localised external pressure urging a portion of the first wall towards the second wall can produce a localised seal.

3. A device according to claim 1 in which an object is retained at a location within the blister.

4. A device according to claim 3 in which the object comprises a dried reagent or a sachet of liquid.

5. A device according to claim 1 in which the first wall is shaped, or has a plurality of dimples, for locating objects at predetermined locations within the blister.

6. A device according to claim 1 in which the second wall has recesses for locating objects.

7. A device according to claim 1, further comprising a sample introduction port to allow introduction of the sample into the blister.

8. A device according to claim 1, further comprising a vacuum port to allow removal of air or a gas from the blister.

9. A device according to claim 1, further comprising a gasket disposed within the blister, in which localised pressure urging the first wall towards the second wall with the gasket in-between can form a localised seal.

10. A device according to claim 9 in which the gasket comprises a material that is disposed on the second wall within the blister to define one or more sealable regions in the blister, the sealable regions being sealable on application of a suitable external force or pressure.

11. A device according to claim 1 in which the blister can be divided into one or more sealed regions by application of one or more shaped platens that urge the first wall towards the second wall.

12. A device according to claim 11 in which the sealed regions can be sealed and unsealed sequentially to allow the sample and/or reagents to pass between the regions in a predetermined manner.

13. A device according to claim 11 in which one or more of the sealed regions contains a processing reagent or processing reagents and removal of the seals allows the sample to contact the processing reagent or reagents.

14. A device according to claim 1 in which the sample may be mixed by an oscillating external pressure applied to at least a portion of the blister.

15. A device according to claim 1, further comprising an analysis means.

16. A device according to claim 15 in which the analysis means is located within a sealable region of the blister.

17. A device according to claim 15 in which the analysis means is located in an analysis chamber in communication with the blister.

18. A device according to claim 17 in which the second wall has an exit port to allow passage of a processed sample from the blister to the analysis chamber.

19. A device according to claim 15 in which the analysis means comprises a test strip.

20. A device according claim 1 in which the second wall is a base plate and the first wall is a flexible film disposed on the base plate.

21. A device according to claim 1 for the processing of a biological, chemical or environmental sample.

22. A device according to claim 1 for the amplification and detection of nucleic acid or genetic material in a biological or environmental sample.

23. A device according to claim 1 in which the blister is sealed from the external environment.

24. A device for the processing of a sample comprising, it single blister only, the blister defining a single cavity and being defined between first and second walls, wherein the first wall is flexible such that the blister can be divided into one or more sealed chambers by an external pressure applied to a portion of the first wall that urges the first wall towards the second wall, the pressure being applied in the form of a two dimensional shape to form a sealed chamber in that shape, wherein the blister, once divided by operation of the external pressure, is operable to become undivided when the external pressure is released.

* * * * *